US012600894B2

(12) United States Patent
Somerville et al.

(10) Patent No.: US 12,600,894 B2
(45) Date of Patent: Apr. 14, 2026

(54) LIGNIN-BASED DRILLING FLUIDS AND RELATED METHODS

(71) Applicant: LignoSol IP Limited, San Gwann (MT)

(72) Inventors: Desmond Alexander Somerville, San Gwann (MT); Patrick Dieter Waibel, San Gwann (MT)

(73) Assignee: LignoSol IP Limited, San Gwann (MT)

( * ) Notice: Subject to any disclaimer, the term of this patent is extended or adjusted under 35 U.S.C. 154(b) by 87 days.

(21) Appl. No.: 18/285,583

(22) PCT Filed: Apr. 5, 2022

(86) PCT No.: PCT/IB2022/053151
§ 371 (c)(1),
(2) Date: Oct. 4, 2023

(87) PCT Pub. No.: WO2022/214954
PCT Pub. Date: Oct. 13, 2022

(65) Prior Publication Data
US 2024/0368448 A1     Nov. 7, 2024

(30) Foreign Application Priority Data

Apr. 6, 2021     (GB) ...................................... 2104883
Nov. 8, 2021     (GB) ...................................... 2115987

(51) Int. Cl.
| | |
|---|---|
| C09K 8/20 | (2006.01) |
| C07G 1/00 | (2011.01) |
| C09K 8/28 | (2006.01) |
| C09K 8/38 | (2006.01) |
| C12P 1/04 | (2006.01) |
| C12R 1/07 | (2006.01) |

(52) U.S. Cl.
CPC ............... *C09K 8/203* (2013.01); *C07G 1/00* (2013.01); *C09K 8/28* (2013.01); *C09K 8/38* (2013.01); *C12P 1/04* (2013.01); *C09K 2208/10* (2013.01); *C12R 2001/07* (2021.05)

(58) Field of Classification Search
CPC . C09K 8/203; C09K 8/28; C09K 8/38; C09K 8/35; C09K 2208/10; C07G 1/00; C12P 1/04; C12R 2001/07
See application file for complete search history.

(56) References Cited

U.S. PATENT DOCUMENTS

| | | | |
|---|---|---|---|
| 3,438,895 | A | 4/1969 | Edmonsond et al. |
| 3,864,276 | A | 2/1975 | Benko et al. |
| 4,101,394 | A | 7/1978 | Johnson |
| 4,133,385 | A | 1/1979 | Kalfoglou |
| 4,304,572 | A | 12/1981 | Wiese et al. |
| 4,392,941 | A | 7/1983 | Roth et al. |
| 4,877,517 | A | 10/1989 | Bulatovic et al. |
| 5,028,238 | A | 7/1991 | von Rybinski et al. |
| 5,059,332 | A | 10/1991 | Satoh |
| 5,114,597 | A | 5/1992 | Rayborn et al. |
| 5,164,480 | A | 11/1992 | Huibers et al. |
| 5,246,602 | A | 9/1993 | Forrest |
| 5,248,329 | A | 9/1993 | Rusin et al. |
| 5,316,664 | A | 5/1994 | Gregoli et al. |
| 5,316,682 | A | 5/1994 | Keyser et al. |
| 5,344,625 | A | 9/1994 | Clough |
| 5,368,972 | A | 11/1994 | Yamashita et al. |
| 5,711,383 | A * | 1/1998 | Terry ....................... C09K 8/16 |
| | | | 507/140 |
| 5,743,945 | A | 4/1998 | Yamashita et al. |
| 5,911,276 | A | 6/1999 | Kieke |
| 6,306,800 | B1 | 10/2001 | Samuel et al. |
| 6,348,436 | B1 | 2/2002 | Langlois et al. |
| 8,450,260 | B2 | 5/2013 | Crawford et al. |
| 8,455,226 | B2 | 6/2013 | De Windt et al. |
| 8,741,256 | B1 * | 6/2014 | Harrison .................. C01D 7/07 |
| | | | 423/427 |
| 8,748,153 | B2 | 6/2014 | Tadic et al. |
| 10,362,786 | B2 | 7/2019 | Chen et al. |
| 10,829,833 | B2 | 11/2020 | Gos et al. |
| 12,275,894 | B2 | 4/2025 | Somerville et al. |
| 2002/0044887 | A1 | 4/2002 | Jones |
| 2006/0177661 | A1 | 8/2006 | Smith et al. |
| 2007/0045198 | A1 | 3/2007 | Sugiura |
| 2009/0011972 | A1 | 1/2009 | Suzuki et al. |

(Continued)

FOREIGN PATENT DOCUMENTS

| | | |
|---|---|---|
| CA | 1132452 A | 9/1982 |
| CA | 2425424 A1 | 4/2002 |

(Continued)

OTHER PUBLICATIONS

Beisl et al., "Lignin from Micro- to Nanosize: Production Methods." Int. Journal of Molecular Sciences. 18(6): 1244 (Jun. 10, 2017) (31 pages).

Bicca et al., "Production of Biosurfactant by Hydrocarbon Degrading Rhodococcus Ruber and Rhodococcus Erythropolis." Revista de Microbiologia. 30: 231-236 (1999) (6 pages).

Chang et al., "A novel nano-lignin-based amphoteric copolymer as fluid-loss reducer in water-based drilling fluids." Colloids and Surfaces A. 583:123979 (Sep. 21, 2019) (10 pages).

Hruzová et al., "Organosolv lignin hydrophobic micro- and nanoparticles as a low-carbon footprint biodegradable flotation collector in mineral flotation." Bioresource Technology. 306:123235 (Mar. 23, 2020) (4 pages).

International Search Report and Written Opinion for International Application No. PCT/IB22/53145 mailed Jun. 27, 2022 (9 pages).

(Continued)

*Primary Examiner* — Aiqun Li

(74) *Attorney, Agent, or Firm* — Clark & Elbing LLP

(57) ABSTRACT

Drilling fluids or muds are provided for the drilling of a borehole into an earth formation. The drilling fluid or mud may be used for drilling oil and/or natural gas wells in subterranean reservoirs. In some embodiments, the fluid is formed from an additive comprising lignin and at least one biosurfactant produced by at least one strain of bacteria capable of biosurfactant production.

16 Claims, No Drawings

(56) References Cited

U.S. PATENT DOCUMENTS

| | | | |
|---|---|---|---|
| 2009/0082227 A1 | 3/2009 | Hnatow et al. | |
| 2009/0211960 A1 | 8/2009 | Nilsen et al. | |
| 2009/0266541 A1 | 10/2009 | Reynolds et al. | |
| 2009/0291861 A1 | 11/2009 | Sawdon | |
| 2009/0308612 A1* | 12/2009 | Weaver | C09K 8/42 |
| | | | 166/305.1 |
| 2010/0137168 A1 | 6/2010 | Quintero et al. | |
| 2010/0233050 A1 | 9/2010 | Gargulak et al. | |
| 2012/0247763 A1 | 10/2012 | Rakitsky et al. | |
| 2013/0274150 A1 | 10/2013 | Holt et al. | |
| 2014/0261077 A1* | 9/2014 | Merck | C08L 95/005 |
| | | | 530/200 |
| 2014/0371071 A1 | 12/2014 | Nitsche | |
| 2015/0166836 A1 | 6/2015 | Liu et al. | |
| 2015/0285051 A1 | 10/2015 | Miller et al. | |
| 2016/0168272 A1 | 6/2016 | Retsina et al. | |
| 2016/0236158 A1 | 8/2016 | Bauer | |
| 2017/0029691 A1 | 2/2017 | Faust, Jr. et al. | |
| 2017/0306264 A1 | 10/2017 | Peggau et al. | |
| 2018/0148632 A1 | 5/2018 | Bennett et al. | |
| 2018/0265794 A1 | 9/2018 | Dahlstrand et al. | |
| 2018/0355446 A1 | 12/2018 | Medoff et al. | |
| 2019/0031945 A1 | 1/2019 | Guo et al. | |
| 2019/0055459 A1 | 2/2019 | Zelenev et al. | |
| 2019/0093463 A1 | 3/2019 | Hardin et al. | |
| 2019/0184350 A1 | 6/2019 | Terasaka et al. | |
| 2019/0382649 A1 | 12/2019 | Jiang et al. | |
| 2019/0390405 A1 | 12/2019 | Geigle et al. | |
| 2020/0032128 A1 | 1/2020 | Farmer et al. | |
| 2020/0157408 A1* | 5/2020 | Farmer | C09K 8/582 |
| 2020/0172788 A1 | 6/2020 | Farmer et al. | |
| 2020/0255466 A1 | 8/2020 | Lintinen et al. | |
| 2020/0352016 A1 | 11/2020 | Bohdy | |
| 2021/0261451 A1 | 8/2021 | Patton | |
| 2021/0261459 A1* | 8/2021 | Alibek | C04B 24/10 |

FOREIGN PATENT DOCUMENTS

| | | | |
|---|---|---|---|
| CA | 2535702 A1 | 3/2005 | |
| CA | 2547100 A1 | 11/2006 | |
| CA | 2640005 A1 | 8/2007 | |
| CA | 2661202 C | 11/2011 | |
| CA | 2723591 C | 7/2013 | |
| CA | 2705147 C | 9/2014 | |
| CA | 2921996 A1 | 3/2015 | |
| CA | 2693008 C | 4/2016 | |
| CA | 2988826 A1 | 12/2016 | |
| CA | 2791256 C | 6/2017 | |
| CA | 3048404 A1 | 7/2018 | |
| CA | 3052048 A1 | 8/2018 | |
| CA | 3052465 A1 | 8/2018 | |
| CA | 3054686 A1 | 9/2018 | |
| CA | 3058761 A1 | 10/2018 | |
| CA | 2999599 C | 12/2019 | |
| CA | 2772395 C | 1/2020 | |
| CA | 2720739 C | 4/2020 | |
| CA | 2950089 C | 4/2020 | |
| CA | 2831902 C | 5/2020 | |
| CA | 2877367 C | 12/2020 | |
| CA | 2945194 C | 7/2022 | |
| CA | 2886934 C | 1/2023 | |
| CN | 85105225 A | 7/1986 | |
| CN | 101104177 A | 1/2008 | |
| CN | 104152129 A | 11/2014 | |
| CN | 104321422 A | 1/2015 | |
| CN | 103636599 B | 3/2015 | |
| CN | 205527917 U | 8/2016 | |
| CN | 106188857 A | 12/2016 | |
| CN | 108441223 A | 8/2018 | |
| CN | 106217826 B | 9/2018 | |
| CN | 108623112 A | 10/2018 | |
| CN | 109943299 A | 6/2019 | |
| CN | 110616062 A | 12/2019 | |
| GB | 2514202 A | 11/2014 | |

| | | | |
|---|---|---|---|
| GB | 2605591 A | 10/2022 | |
| JP | 2011-121002 A | 6/2011 | |
| JP | 2017029892 A | 2/2017 | |
| KR | 101711607 B1 | 3/2017 | |
| KR | 10-2018-0130070 A | 12/2018 | |
| RU | 2188935 C1 | 9/2002 | |
| WO | WO-1992/19349 A1 | 11/1992 | |
| WO | WO-2005/028592 A1 | 3/2005 | |
| WO | WO-2012/151524 A2 | 11/2012 | |
| WO | WO-2013/037643 A1 | 3/2013 | |
| WO | WO-2015/065981 A1 | 5/2015 | |
| WO | WO-2016/053345 A1 | 4/2016 | |
| WO | WO-2016/196680 A1 | 12/2016 | |
| WO | WO-2018/064689 A1 | 4/2018 | |
| WO | WO-2019/067356 A1 | 4/2019 | |
| WO | WO-2019/112970 A1 | 6/2019 | |
| WO | WO-2019/191296 A1 | 10/2019 | |
| WO | WO-2019/213055 A1 | 11/2019 | |
| WO | WO-2020/028253 A1 | 2/2020 | |
| WO | WO-2020/060529 A1 | 3/2020 | |
| WO | WO-2020/072735 A1 | 4/2020 | |
| WO | WO-2020/149756 A2 | 7/2020 | |
| WO | WO-2020/264073 A1 | 12/2020 | |
| WO | WO-2021/015633 A1 | 1/2021 | |
| WO | WO-2021/052939 A1 | 3/2021 | |

OTHER PUBLICATIONS

International Search Report and Written Opinion for International Application No. PCT/IB22/53147 mailed Jun. 15, 2022 (9 pages).
International Search Report and Written Opinion for International Application No. PCT/IB22/53148 mailed Jun. 27, 2022 (9 pages).
International Search Report and Written Opinion for International Application No. PCT/IB22/53151 mailed Jun. 29, 2022 (9 pages).
International Search Report and Written Opinion for International Application No. PCT/IB22/53158 mailed Jun. 21, 2022 (8 pages).
International Search Report and Written Opinion for International Application No. PCT/IB22/53160 mailed Jun. 29, 2022 (7 pages).
International Search Report and Written Opinion for International Application No. PCT/IB22/53161 mailed Jun. 27, 2022 (6 pages).
International Search Report and Written Opinion for International Application No. PCT/IB22/53162 mailed Jul. 1, 2022 (7 pages).
Li, Qingxin, "Rhamnolipid synthesis and production with diverse resources." Front. Chem. Sci. Eng. 11(1): 27-36 (Mar. 22, 2017) (10 pages).
Negi et al., "A review on lignin utilization in petroleum exploration, petroleum products formulation, bio-fuel production, and oil spill clean-up." Biomass Conversion and Biorefinery. 13: 1417-1428 (Nov. 5, 2020) (12 pages).
Sauki et al., "Extracted Lignin from Rhizophora's Black Liquor as Fluid Loss Control Additive in Water Based Drilling Mud." Key Engineering Materials. 755: 74-80 (Aug. 20, 2018) (8 pages).
Schneider et al., "Assessment of Morphological, Physical, Thermal, and Thermal Conductivity Properties of Polypropylene/ Lignosulfonate Blends." Materials. 14(3): 543 (Jan. 23, 2021) (10 pages).
Search and Examination Report for Application No. GB2104859.0, dated May 11, 2021 (8 pages).
Search and Examination Report for Application No. GB2104860.8, dated May 4, 2021 (8 pages).
Search and Examination Report for Application No. GB2104862.4, dated May 21, 2021 (8 pages).
Search and Examination Report for Application No. GB2104865.7, dated Jun. 8, 2021 (8 pages).
Search and Examination Report for Application No. GB2104869.9, dated Apr. 16, 2021 (6 pages).
Search and Examination Report for Application No. GB2104870.7, dated Jun. 2, 2021 (7 pages).
Search and Examination Report for Application No. GB2104877.2, dated May 10, 2021 (6 pages).
Search and Examination Report for Application No. GB2104883.0, dated May 4, 2021 (8 pages).
Search and Examination Report for Application No. GB2115987.6, dated Dec. 15, 2021 (6 pages).

(56) References Cited

OTHER PUBLICATIONS

Solihat et al., "Lignin as an Active Biomaterial: A Review." Jurnal Sylva Lestari. 9(1): 1-22 (Jan. 2021) (22 pages).

EP Application No. EP4320192, Extended European Search Report (EESR), Search Opinion, and Supplementary Search Report, dated Jan. 17, 2025 (11 pages).

GB Application No. GB2116007.2, Search and Examination Report, dated Nov. 25, 2021 (8 pages).

GB Application No. GB2214123.8, Search and Examination Report, dated Nov. 18, 2022 (8 pages).

PCT Application No. PCT/IB22/59176, International Search Report (ISR) and Written Opinion, mailed Jan. 26, 2023 (9 pages).

PCT Application No. PCT/IB23/59500, International Search Report (ISR) and Written Opinion, mailed Feb. 2, 2024 (8 pages).

Nazari et al., "Study relationships between flotation variables and recovery of coarse particles in the absence and presence of nanobubble," Colloids and Surfaces A: Physicochemical and Engineering Aspects 559:284-8 (Sep. 27, 2018).

Schneider et al., "Assessment of Morphological, Physical, Thermal, and Thermal Conductivity Properties of Polypropylene/ Lignosulfonate Blends", Materials, (Jan. 2021) vol. 14: 543 (10 pages).

Madhu, "Difference Between Anolyte and Catholyte", published Online Sep. 19, 2020 at: https://www.differencebetween.com/difference-between-anolyte-and-catholyte/ (3 pages).

This vs. That: Anolyte vs. Catholyte, published Online at: https://thisvsthat.io/anolyte-vs-catholyte (2023) (2 pages).

Arapova et al., "Lignin: A Renewable Resource of Hydrocarbon Products and Energy Carriers (Review)", Petrochemistry. (2020) vol. 60, No. 3, pp. 251-269 (English Translation) (38 pages).

Filonov et al., "Bioremediation of Oil-Contaminated Soils in the Republic of Belarus Using the Biopreparation 'Microbak' and a Sorbent based on Lignin", Puschchino Conference Proceedings: Biochemistry, Physiology and Biosphere the Role of Microorganisms, Dec. 2-6, 2019 (English Translation) (8 pages).

Lazareva et al., "Pseudomonas aeruginosa: Pathogenicity, Pathogenesis and Diseases", (English Abstract Only) (2015) vol. 17, No. 3, pp. 170-184 (17 pages).

Saikia et al., "Isolation of biosurfactant-producing Pseudomonas aeruginosa RS29 from oil-contaminated soil and evaluation of different nitrogen sources in biosurfactant production", Ann. Microbiol. (Jul. 2011) vol. 62, pp. 753-763 (11 pages).

* cited by examiner

LIGNIN-BASED DRILLING FLUIDS AND RELATED METHODS

CROSS-REFERENCE TO RELATED APPLICATIONS

This application claims priority to GB Provisional Patent Application No. 2104883.0, filed 6 Apr. 2021, and GB Provisional Patent Application No. 2115987.6, filed 8 Nov. 2021, the disclosures of which are hereby incorporated by reference in their entireties.

BACKGROUND OF THE INVENTION

The present disclosure relates to drilling fluids. More particularly, the present disclosure relates to lignin-based drilling fluids for oil and gas drilling operations and related methods.

Drilling fluids, also known as drill muds, are used in drilling oil and natural gas wells, with their main function being to carry cuttings out of the drill hole. Several broad types of drilling fluids are used, including so-called water-based muds (WBMs), oil-based muds (OBMs), gaseous drilling fluids and synthetic-based muds (SBMs), for example.

In operation, the drilling fluid is pumped through the drill string, spraying out of nozzles on the drill bit, which cleans and cools the drill bit, returning along the annular space between the drill bit and the wall of the borehole or well, carrying the cuttings to the surface.

Water based drilling fluids contain modified starches and carboxymethylcellulose (CMC) for filtrate control (and clay encapsulation), partially hydrolyzed polyacrylamide (PHPA) for clay encapsulation and a viscosity modifier, such as Xantham Gum (XC/XCD). These polymers are acid soluble and biodegradable, thereby vulnerable to sulfate reducing bacteria in particular at pH<9. For this reason a biocide is normally added to the drilling fluid. Synthetic polymers are an alternative but expensive and not biodegradable to the same standard.

Two important considerations for any drilling fluid are exacting filtrate control and stable, predictable rheology. There is also a fine balance between using a thin, low rheology fluid to avoid undue pressures on the wellbore, whilst ensuring the density of the drilling fluid is such as to support the carrying of cuttings to the surface. KCl is often added for clay/shale control and/or saturated NaCl is often added when drilling through salt formations.

By far the biggest drilling fluid contaminants are drilled formation fines and the operation is geared to keep these under control by avoiding turbulent annular flow, efficient screening, hydrocyclones and centrifuging. Other potential contaminants from the formation are $CO_2$ and $H_2S$, which are best contained by pH>10 and in the case of severe $H_2S$ contamination by the addition of dedicated scavengers.

SUMMARY OF THE INVENTION

In one aspect of the invention, there is provided a drilling fluid or mud suitable for drilling a borehole, well or the like in to an earth formation, in particular a subterranean reservoir for recovering hydrocarbons from the reservoir, the drilling fluid or mud comprising lignin and at least one isolated strain of bacteria capable of producing at least one biosurfactant, and/or at least one biosurfactant produced from at least one bacteria capable of producing a biosurfactant, the drilling fluid or mud having a solids content of above about 55%, in particular of about 55% to about 60%.

In some embodiments, the lignin is technical lignin.

In some embodiments, the technical lignin comprises at least one of Kraft lignin, lignosulfonates, soda lignin, organosolv lignins, steam-explosion lignin, enzymatic hydrolysis lignin, or unhydrolyzed Kraft black liquor lignin.

In some embodiments, the lignin is in an aqueous suspension.

In some embodiments, the lignin comprises at least one of lignin nanoparticles and lignin microparticles.

In some embodiments, the lignin and at least one biosurfactant are provided as an additive.

In some embodiments, the at least one biosurfactant is produced by contacting the lignin with the at least one strain of bacteria capable of producing the at least one biosurfactant, any live bacteria being removed from the additive prior to constitution of the drilling fluid or mud.

In some embodiments, the at least one strain of bacteria is at least one isolated strain of *Bacillus*.

In some embodiments, the at least one isolated strain is in the form of a liquid suspension or freeze-dried spores.

In some embodiments, the additive further comprises a catholyte solution.

In some embodiments, the catholyte solution is a stabilized or upgraded catholyte solution.

In some embodiments, the additive further comprises at least one of a carboxylic acid or a salt or ester thereof.

In some embodiments, the carboxylic acid ester comprises a methyl ester or a butyl ester.

In some embodiments, the carboxylic acid or salt or ester thereof comprises a di-carboxylic acid or a salt or ester thereof.

In some embodiments, the additive further comprises carbon black.

In some embodiments, the additive further comprises pyrolysis oil.

In some embodiments, the additive is gasified.

In some embodiments, the additive is gasified with at least one of nanobubbles and microbubbles.

In another aspect, there is provided a use of an additive comprising lignin and at least one isolated strain of bacteria capable of biosurfactant production in a drilling fluid application.

Other aspects and features of the present disclosure will become apparent, to those ordinarily skilled in the art, upon review of the following description of specific embodiments of the disclosure.

DESCRIPTION OF PREFERRED EMBODIMENTS

The drilling fluids of the invention, in particular lignin-based drilling fluids, are provided for drilling boreholes, wells or the like into subterranean reservoirs for recovering hydrocarbons from the reservoirs.

As used herein, "drilling fluid" or "drilling mud" refers to the fluid used with a drill rig to carry excavated rock or cuttings, produced by a drill bit drilling a borehole or well into the earth formation, to the surface for further processing.

As used herein, "lignin" refers to a biopolymer that is found in the secondary cell wall of plants and some algae. Lignin is a complex cross-linked phenolic polymer with high heterogeneity. Typical sources for the lignin include, but are not limited to: softwood; hardwood; and herbaceous plants such as corn stover, bagasse, grass, and straw, for example.

In some embodiments, the lignin comprises technical lignin. As used herein, "technical lignin" refers to lignin that has been isolated from lignocellulosic biomass, for example, as a byproduct of a pulp and paper production or a lignocellulosic biorefinery. Technical lignins may have a modified structure compared to native lignin and may contain impurities depending on the extraction process. In some embodiments, the technical lignin comprises at least one of Kraft lignin, lignosulfonates, soda lignin, organosolv lignin, steam-explosion lignin, and enzymatic hydrolysis lignin. In other embodiments, the technical lignin may comprise any other form of technical lignin.

In embodiments where the lignin comprises lignosulfonates, the lignosulfonates may be in the form of a salt including, for example, sodium lignosulfonate, calcium lignosulfonate, or ammonium lignosulfonate.

In other embodiments, the technical lignin is in the form of unhydrolyzed Kraft black liquor. Black liquor is a byproduct of the Kraft process and may contain not only lignin but hemicellulose, inorganic chemicals used in the pulping process, and other impurities. In other embodiments, the technical lignin is in the form of "brown liquor" (also referred to as red liquor, thick liquor and sulfite liquor) which refers to the spent liquor of the sulfite process. In other embodiments, the technical lignin may be in the form of any other spent cooking liquor of a pulping process or any other suitable lignin-based byproduct.

In other embodiments, the lignin may be synthetic lignin or any other suitable type of lignin.

In some embodiments, the lignin is hydrolyzed. As used herein, "hydrolyze" refers to using acid or base hydrolysis to at least partially separate lignin from the polysaccharide content of the lignocellulosic biomass. For example, where the lignin is in the form of black liquor, carbon dioxide may be used to precipitate Kraft lignin from the black liquor and then the Kraft lignin may be neutralized with sodium hydroxide.

In some embodiments, the lignin is in aqueous suspension. As used herein, an "aqueous suspension" of lignin refers to solid particles of lignin suspended, dispersed, and/or dissolved in a solvent that at least partially comprises water. In some embodiments, the solvent comprises substantially all water. In other embodiments, the solvent may comprise a combination of water and any other suitable solvent.

In some embodiments, the aqueous suspension of lignin may have a solids content of about 10% to about 75%, or about 25% to about 70%, or about 30% to about 60%, or about 33% to about 55% or about 50% to about 60% or about 55% to about 60%. In some embodiments, the aqueous suspension of lignin may have a solids content of about 10% or above, or of about 25% or above, or of about 30% or above, or of about 33% or above or of about 50% or above or of about 55% or above. In some embodiments, the aqueous suspension of lignin may have a solids content of about 75% or below, or of about 70% or below, or of about 60% or below, or of about 55% or below. The higher solids content in the drilling mud of the invention significantly reduces or eliminates heat transfer to the drill string.

In some embodiments, the lignin comprises at least one of lignin nanoparticles and lignin microparticles. As used herein, "nanoparticle" refers to a particle in the nanometer size range, for example, between about 1 nm and about 100 nm, and "microparticle" refers to a particle in the micrometer size range, for example, between about 100 nm and about 1000 μm (1 mm). In some preferred embodiments, the lignin particles have a size of about 200 nm or less, or about 100 nm or less. In some preferred embodiments, at least about 20%, or at least 30%, or at least 40%, or at least 50%, or at least 60%, or at least 70%, or at least 80%, or at least 90% of the lignin particles are nanoparticles having a size of about 100 nm or less.

The lignin nanoparticles and/or microparticles can be produced by any suitable method. For example, the lignin nanoparticles and/or microparticles can be produced using at least one of: solvent shifting; pH shifting; cross-linking polymerization; mechanical treatment; ice-segregation; template based synthesis; aerosol processing; electro spinning; and carbon dioxide ($CO_2$) antisolvent treatment. Such methods are described in Beisl et al. "Lignin from Micro- to Nanosize: Production Methods" *Int. J. Mol. Sci.* 2017; 18: 1244, incorporated herein by reference in its entirety.

In some preferred embodiments, lignin nanoparticles are produced using a pH shifting method, for example, as disclosed in Beisl et al. Briefly, the starting lignin material may be dissolved in a basic solution (e.g. an aqueous NaOH solution at pH 12) and the pH of the solution may be gradually decreased by addition of acid (e.g. $HNO_3$) to precipitate lignin nanoparticles. The solution may then be neutralized (e.g. by addition of NaOH) to resuspend the nanoparticles. The resulting particles may have a size of about 200 nm or less, or about 100 nm or less. In other embodiments, the lignin nanoparticles may be produced by any other suitable method.

By providing the lignin in the form of lignin nanoparticles and/or microparticles, the surface area of the lignin is increased, thereby also increasing the negative force around each particle. In addition, lignin nanoparticles and/or microparticles may have improved solubility in water. Conventional lignins are typically only soluble in water at alkaline pH; however, nanoparticles and/or microparticles may be soluble in approximately neutral water (Beisl et al.), which may be preferred for some applications.

In some embodiments, where the lignin comprises an aqueous suspension of lignin nanoparticles, the zeta potential value of the suspension may be about −5 to about −80 mV. In some embodiments, the specific gravity of the aqueous suspension of lignin nanoparticles is between about 1.286 to about 1.7 SG.

In some embodiments, the lignin and at least one biosurfactant produced by at least one isolated strain of bacteria capable of biosurfactant production are provided as an additive. As used herein, "isolated" or "isolate", when used in reference to a strain of bacteria, refers to bacteria that have been separated from their natural environment. In some embodiments, the isolated strain or isolate is a biologically pure culture of a specific strain of bacteria. As used herein, "biologically pure" refers to a culture that is substantially free of other organisms.

As used herein, "biosurfactant" refers to compounds that are produced at the bacterial cell surface and/or secreted from the bacterial cell and function to reduce surface tension and/or interfacial tension. Non-limiting examples of biosurfactants include: lipopeptides, surfactin, glycolipids, rhamnolipids, methyl rhamnolipids, viscosin, and the like. The isolated strain may be capable of producing one or more types of biosurfactants.

In some embodiments, the isolated strain may produce one or more additional active compounds. For example, the isolated strain may produce a biopolymer, solvent, acid, exopolysaccharide, or the like.

In some embodiments, the at least one isolated strain of bacteria comprises a strain of *Bacillus*. In other embodiments, the at least one isolated strain comprises a strain of bacteria capable of biosurfactant production and that is non-pathogenic. Non-limiting examples of suitable strains are listed in Satpute et al. "Methods for investigating bio-surfactants and bioemulsifers: a review" *Critical Reviews in Biotechnology*, 2010, 1-18. For example, the at least one isolated strain of *Bacillus* may be *Bacillus amyloliquefaciens, Bacillus licheniformis, Bacillus pumilus, Bacillus subtilis*, or combinations thereof, in particular *Bacillus licheniformis*.

In some embodiments, the pH of the additive may be selected or adjusted to provide a suitable pH for the isolated strain(s). In some embodiments, the additive may further comprise one or more nutrients to support growth of the bacteria such as, for example, acetate, one or more vitamins, or the like.

In some embodiments, the isolated strain is in a viable form. For example, in some embodiments, the isolated strain may be in the form of a liquid suspension. In some embodiments, the isolated strain may be incubated for a suitable period of time prior to incorporation into the additive such that at least a portion of biosurfactant(s) are secreted into bacterial suspension and therefore can be incorporated into the additive. For example, the bacteria can be incubated/fermented for between about one day and about six months or longer. The isolated strain may be incubated in the presence of a nutrient source and under suitable conditions (e.g. temperature, agitation, etc.) to produce the biosurfactant(s).

In other embodiments, the isolated strain may be in a lyophilized (freeze-dried) form. In some embodiments, the freeze-dried form comprises freeze-dried spores.

In some embodiments, where the isolated strain is in the form of a liquid suspension or in a freeze-dried form, the composition may comprise approximately 40 billion CFU (colony forming units) may be combined with at least about 1 g of lignin and up to several tons of lignin.

In other embodiments, the isolated strain may in an inviable form. For example, the isolated strain may be in the form of heat-killed cells or a cell lysate. In these embodiments, the bacteria of the isolated strain may be incubated for a suitable period of time prior to loss of viability (e.g. heat killing or lysis) such that a sufficient quantity of biosurfactant(s) is secreted into the bacterial suspension for incorporation into the additive. For example, the bacteria may be incubated for at least one week prior to loss of viability.

In other embodiments, a liquid suspension of bacteria may be incubated to produce the biosurfactant(s) and a supernatant containing the biosurfactant(s) may be separated from the bacterial cells and used in the additive.

Without being limited by theory, it is believed that the combination of lignin and the biosurfactant produced by the isolated strain act to mimic the natural habitat of the biosurfactant producing strains. The lignin may function as a growth substrate that contains required nutrients (carbon and fructose) to support growth of the bacteria, with the exception of additional acetate and metallic vitamins which may be added to the additive as needed.

In addition, a series of drop collapse tests were conducted to evaluate additional benefits of combining the lignin with a suitable biosurfactant in the composition of the invention. In particular, the tests were carried out to determine the effectiveness of the compositions of the invention in reducing the surface tension of water and other liquids. The results indicated that a further advantage in combining the lignin and biosurfactant in the composition of the invention is a significant reduction in surface tension at concentrations of between about 10 ppm and 300 ppm of the biosurfactant, which assists significantly in the compositions ability to cut through hydrocarbon containing materials.

In some embodiments, the lignin-based additives of the invention further comprise catholyte solutions. As used herein, "catholyte solution" is an activated solution produced in an electrochemical reaction, and is that part of the electrolyte solution adjacent the cathode of an electrochemical cell. It can be produced, for instance, from a 0.05%-1% salt brine (NaCl or KCl), and has a pH in the range 10.0 to 13.0 and an ORP/Redox value of less than about –800 mV, typically in the order of –900 to –950 mV. In the case of an NaCl starting solution, the active ingredient is highly active, and typically unstable, NaOH.

The additive of the invention can comprise from about 1% to about 75% by volume of the catholyte solution.

In some embodiments, the additive further comprises at least one of a carboxylic acid or a salt or ester thereof. In some embodiments, the carboxylic acid is a di-carboxylic acid or a salt or ester thereof. The carboxylic acid or salt/ester thereof may function as a solvent, for example, by facilitating formation of a stable emulsion of the various components of the additive. In some embodiments, the additive comprises a carboxylic acid ester. In some embodiments, the carboxylic acid ester comprises a methyl ester or a butyl ester. In some embodiments, the butyl esters are produced by biochemical metathesis. In some embodiments, the butyl ester comprises n-Butyl 4-oxopentanoate. In some embodiments, the methyl ester comprises unsaturated $C_{10}$ or $C_{12}$ methyl ester. In some embodiments, the methyl ester comprises methyl 9-decenoate or methyl 9-dodecenoate. In some embodiments, the methyl ester is produced from a plant oil feedstock.

In other embodiments the carboxylic acid or a salt or ester thereof may comprise at least one oleic acid or a salt or ester thereof. In some embodiments, the oleic acid or a salt or ester thereof may be provided in the form of "tall oil", a viscous liquid obtained as a byproduct of the Kraft process. In some embodiments, the tall oil may be distilled to tall oil rosin or tall oil fatty acid (TOFA) which comprise a higher proportion of oleic acids than tall oil.

In some embodiments, the additive comprises a combination of two or more carboxylic acids or salts/esters thereof. As one example, the additive may comprise a combination of di-carboxylic acid and butyl esters produced by biochemical metathesis.

In some embodiments, the additive may comprise about 1% to about 30%, or about 1% to about 20%, or about 1% to 10% of di-carboxylic acid and/or butyl esters by volume.

In some embodiments, the additive further comprises carbon black. The carbon black may be electroconductive carbon black and the carbon black may function to increase the conductivity of the additive. In some embodiments, the carbon black may be conductive, superconductive, extraconductive or ultraconductive carbon black. In some embodiments, the carbon black may be in the form of carbon black beads, microparticles, and/or nanoparticles. For example, the carbon black may comprise Printex™ XE2 B Beads from Orion Engineered Carbons™. In some embodiments, the additive may comprise about 0.5% to about 10% carbon black by volume. In some embodiments, addition of carbon black may increase the negative zeta potential of the additive thereby increasing its electrical stability. In other embodiments, the additive may comprise any other highly conductive microparticle and/or nanoparticle.

In some embodiments, the additive is gasified with a gas. As used herein, "gasified" refers to introduction of a gas into the lignin such that bubbles of the gas are suspended therein. The term "aerated" refers to gasifying with air or oxygen. The gas may be selected based on the aerobic or anaerobic nature of the isolated strain(s) incorporated into the additive. In some embodiments, the gas at least partially comprises oxygen. For example, the gas may be air or relatively pure oxygen. In some embodiments, the gas may at least partially comprise carbon dioxide and/or nitrogen. Gasification may function to provide oxygen and/or other suitable gasses directly or in close proximity to the bacterial cells of the isolated strain. Gasification may promote proliferation of the bacterial cells and allow the additive to be used or stored for an extended period of time. In some embodiments, the aerated additive may have a half-life of about 20 to 30 days.

In some embodiments, the additive is gasified with nanobubbles and/or microbubbles of the gas. As used herein, "nanobubble" refers to bubbles in the nanometer range and "microbubble" refers to bubbles in the micrometer range. The nanobubbles and/or microbubbles may be introduced into the additive by any suitable means including, for example, a micro- or nanobubble nozzle or a venturi tube.

It has surprisingly been found that using a stabilized or upgraded as opposed to an otherwise unstable catholyte solution enhances the action of the additives of the invention. Accordingly, in some embodiments, the catholyte solution is pre-treated in a system that is designed to introduce nitrogen gas into the catholyte solution, in particular in the form of nano- and/or micro-bubbles, for incorporation into a composition of the invention.

Accordingly, in some embodiments, the catholyte solution is upgraded prior to blending with the other components of the additive.

In some embodiments, the additive may comprise any other suitable components. For example, in some embodiments, the additive may further comprise at least one nutrient source for the live bacteria of the isolated strain.

At +/−1.3 SG, the density of the additive is potentially too high for some drilling fluid applications. It is, therefore, in some embodiments, provided at 5-10% by volume sans bacteria when constituting the drilling fluid or mud. In other embodiments, the additive may provide a suitable drilling fluid base in hole intervals where densities of ≥1.3 SG are required from the start, saving on the cost of barite additions.

A number of potential benefits of using lignin based drilling fluids or muds include enhance wellbore lubricity, contribution to filtration control (possibly together with other additives), improved shale inhibition and cuttings integrity, and improved cuttings separation, and improved corrosion control (as the *Bacillus* strains inhibit sulphate reducing bacteria), for example.

Therefore, in some embodiments, a relatively non-toxic, inert, and sustainable additive is provided for producing a drilling fluid. The additive may also be relatively low cost as lignin is a waste product of pulp and paper operations that is typically discarded.

Various modifications besides those already described are possible without departing from the concepts disclosed herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although particular embodiments have been shown and described, it will be appreciated by those skilled in the art that various changes and modifications might be made without departing from the scope of the disclosure. The terms and expressions used in the preceding specification have been used herein as terms of description and not of limitation, and there is no intention in the use of such terms and expressions of excluding equivalents of the features shown and described or portions thereof.

The invention claimed is:

1. A drilling fluid or mud suitable for drilling a borehole, or well into an earth formation, the drilling fluid or mud comprising an aqueous suspension of solid lignin particles and at least one isolated strain of *Bacillus* selected from the group consisting of *Bacillus amyloliquefaciens, Bacillus licheniformis, Bacillus pumilus, Bacillus subtilis*, and combinations thereof, the drilling fluid or mud having a solid content of above about 55%, wherein the aqueous suspension of solid lignin particles has a solid content of solid lignin particles of about 25% or above.

2. The drilling fluid or mud of claim 1, wherein a source of the lignin solid particles is technical lignin.

3. The drilling fluid or mud of claim 2, wherein the technical lignin comprises at least one of Kraft lignin, lignosulfonates, soda lignin, organosolv lignins, steam-explosion lignin, enzymatic hydrolysis lignin, or unhydrolyzed Kraft black liquor lignin.

4. The drilling fluid or mud of claim 1, wherein the solid lignin particles comprise at least one of lignin nanoparticles and lignin microparticles.

5. The drilling fluid or mud of claim 1, wherein at least 20% of the solid lignin particles are lignin nanoparticles.

6. The drilling fluid or mud of claim 1, wherein the solid lignin particles and the at least one biosurfactant are provided as an additive.

7. The drilling fluid or mud of claim 6, wherein the at least one isolated strain of *Bacillus* bacteria is in the form of a liquid suspension or freeze-dried spores.

8. The drilling fluid or mud of claim 6, wherein the additive further comprises a stabilized or enhanced catholyte solution, wherein the catholyte solution is enhanced or stabilized in a pre-treatment system arranged to introduce nitrogen gas, in the form of nanobubbles and/or microbubbles, into the catholyte solution.

9. The drilling fluid or mud of claim 6, wherein the additive further comprises at least one of a carboxylic acid or a salt or ester thereof.

10. The drilling fluid or mud of claim 6, wherein the additive further comprises carbon black.

11. The drilling fluid or mud of claim 6, wherein the additive further comprises pyrolysis oil.

12. The drilling fluid or mud of claim 6, wherein the additive is gasified.

13. The drilling fluid or mud of claim 12, wherein the additive is gasified with at least one of nanobubbles and microbubbles.

14. The drilling fluid or mud of claim 1, which has a solid content of about 55% to about 60%.

15. A drilling fluid or mud suitable for drilling a borehole or well into an earth formation, the drilling fluid or mud comprising an aqueous suspension of solid lignin particles and at least one isolated strain of bacteria capable of producing at least one biosurfactant, the aqueous suspension of solid lignin particles comprising lignin nanoparticles and microparticles and having a solid content of solid lignin particles of about 55% or above.

16. The drilling fluid or mud of claim 15, wherein the at least one isolated strain of bacteria is selected from the group consisting of *Bacillus amyloliquefaciens, Bacillus licheni-formis, Bacillus pumilus, Bacillus subtilis,* and combinations thereof.

\* \* \* \* \*